(12) United States Patent
Radak

(10) Patent No.: US 6,427,080 B1
(45) Date of Patent: Jul. 30, 2002

(54) CERVICAL SPINE GAUGE AND PROCESS

(76) Inventor: Richard E. Radak, N3025 Lake Forest Cir., Lake Geneva, WI (US) 53147

(*) Notice: Subject to any disclaimer, the term of this patent is extended or adjusted under 35 U.S.C. 154(b) by 0 days.

(21) Appl. No.: 09/572,011

(22) Filed: May 16, 2000

(51) Int. Cl.[7] .............................................. A61B 5/103
(52) U.S. Cl. ..................... 600/425; 600/594; 600/587; 33/511; 33/512
(58) Field of Search ..................... 600/425, 587, 600/594; 283/70, 900; 378/164, 163, 165; 33/511, 512

(56) References Cited

U.S. PATENT DOCUMENTS

| | | | | |
|---|---|---|---|---|
| 5,181,525 A | * | 1/1993 | Bunnell | 600/594 |
| 5,471,995 A | * | 12/1995 | Halliday | 35/514.2 |
| 5,583,663 A | * | 12/1996 | Boeve | |
| 5,832,422 A | | 11/1998 | Wiedenhoefer | |

\* cited by examiner

*Primary Examiner*—Marvin M. Lateef
*Assistant Examiner*—Teoyuh Lin
(74) *Attorney, Agent, or Firm*—Ryan Kromholz & Manion, S.C.

(57) ABSTRACT

A guide for assisting a health care practitioner in evaluating radiographic images of spines is based on a flexible transparent sheet bearing images thereon which each include an edge representing the periphery of a vertebra and a line inscribed thereon laterally displaced from the edge by a measured distance which represents the maximum thickness of soft tissue allowed in the absence of a cervical spinal injury for each corresponding cervical vertebra. A process for evaluating a radiographic image of a spine involves placing the guide over a lateral radiographic image of a subject spine that is to be evaluated with the edge representing the periphery of a selected vertebra placed in alignment with the radiographic image of the corresponding selected cervical vertebra. The amount of soft tissue appearing in radiographic image is observed in relation to the line and thereby determining whether the amount of soft tissue present exceeds a soft tissue allowance for the specific vertebra.

4 Claims, 4 Drawing Sheets

CERVICAL SPINE GAUGE AND PROCESS

The present invention relates to a gauge or guide device for assisting health care practitioners in evaluating radiographic images of a spine and to processes for using such devices.

BACKGROUND OF THE INVENTION

Health care practitioners such as physicians, radiologists, chiropractors, and physician's assistants often analyze radiographic films in the evaluation of possible injuries suffered by the subject patient. Such radiographic films, commonly referred to as "x-rays" are especially analyzed in relation to detection and evaluation of cervical spine injuries. Heretofore simple instruments such as rulers or the like have been used to measure the soft tissue present adjacent to the edges on the vertebrae. Also the evaluation process tends to be dependant on the memory of the particular health care practitioner, thereby introducing the possibility of errors, especially during times of stress, caused, for example by heavy work load or emergencies.

SUMMARY OF THE INVENTION

It is a principal object of the present invention to provide an improved guide for assisting health care practitioners in the evaluation of radiographic images of the spine. In accordance with one aspect of the invention a flexible transparent plastic sheet is utilized as a base substrate for the guide. In accordance with a related aspect, the substrate has inscribed thereon at least one and preferably a number of images, each representing at least the peripheries of a number of individual vertebrae being evaluated.

In accordance with a further related aspect, each of the images representing the peripheral edge of a vertebra is provided with an associated line on the substrate laterally displaced from the image representing the vertebra. The line is displaced at a distance representing the maximum thickness of soft tissue allowed or expected to exist for a specific vertebra in the absence of a spinal injury. Thus the health care practitioner can overlay the peripheral edge of the image which represents a vertebra over the radiographic image and accurately judge whether or not the allowable thickness of soft tissue has been exceeded, in which event an injury is suspected to have occurred in the vicinity of the vertebra.

In accordance with further aspects of the invention, various additional inscriptions are provided on the substrate with appropriate labeling indicating alignment of or measurements for additional characteristics of the images being evaluated, for example, "spinous processes" and "hangman's" which additional measurements are used to assess additional radiographic areas.

Briefly, the invention provides a guide for assisting a health care practitioner in evaluating radiographic images of spines which is based on a flexible transparent sheet bearing images thereon. The images each include an edge representing the periphery of a vertebra and a line inscribed thereon laterally displaced from the edge by a measured distance which represents the maximum thickness of soft tissue allowed in the absence of a cervical spinal injury for each corresponding cervical vertebra. A process for evaluating a radiographic image of a spine involves placing the guide over a lateral radiographic image of a subject spine that is to be evaluated with the edge representing the periphery of a selected vertebra placed in alignment with the radiographic image of the corresponding selected cervical vertebra. The amount of soft tissue appearing in radiographic image is observed in relation to the line and thereby determining whether the amount of soft tissue present exceeds a soft tissue allowance for the specific vertebra.

Further aspects of the invention will be apparent from the accompanying claims, the following detailed description and the drawings.

DETAILED DESCRIPTION OF THE INVENTION

Figure 1:
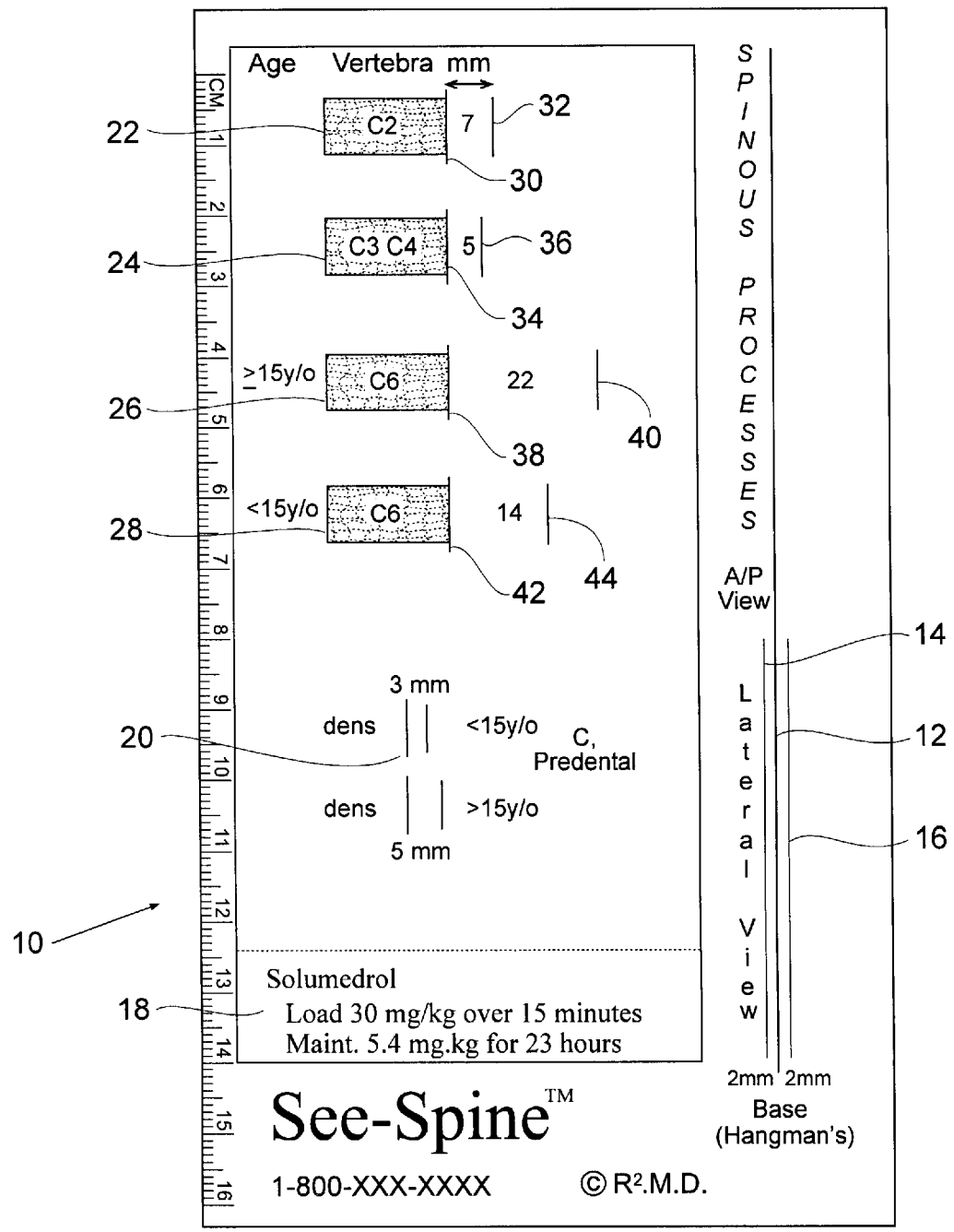
FIG. 1 is a top plan view of a cervical spine gauge of the invention.
Figure 2:
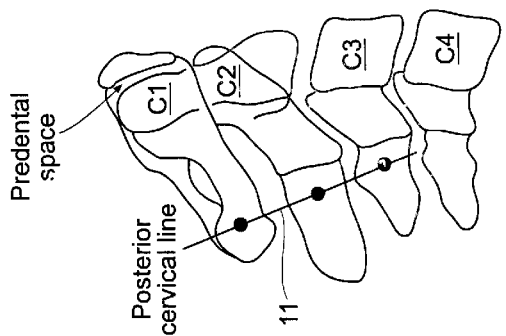
FIG. 2 is a fragmentary lateral view of a segment of a human cervical spine viewed laterally.
Figure 4:
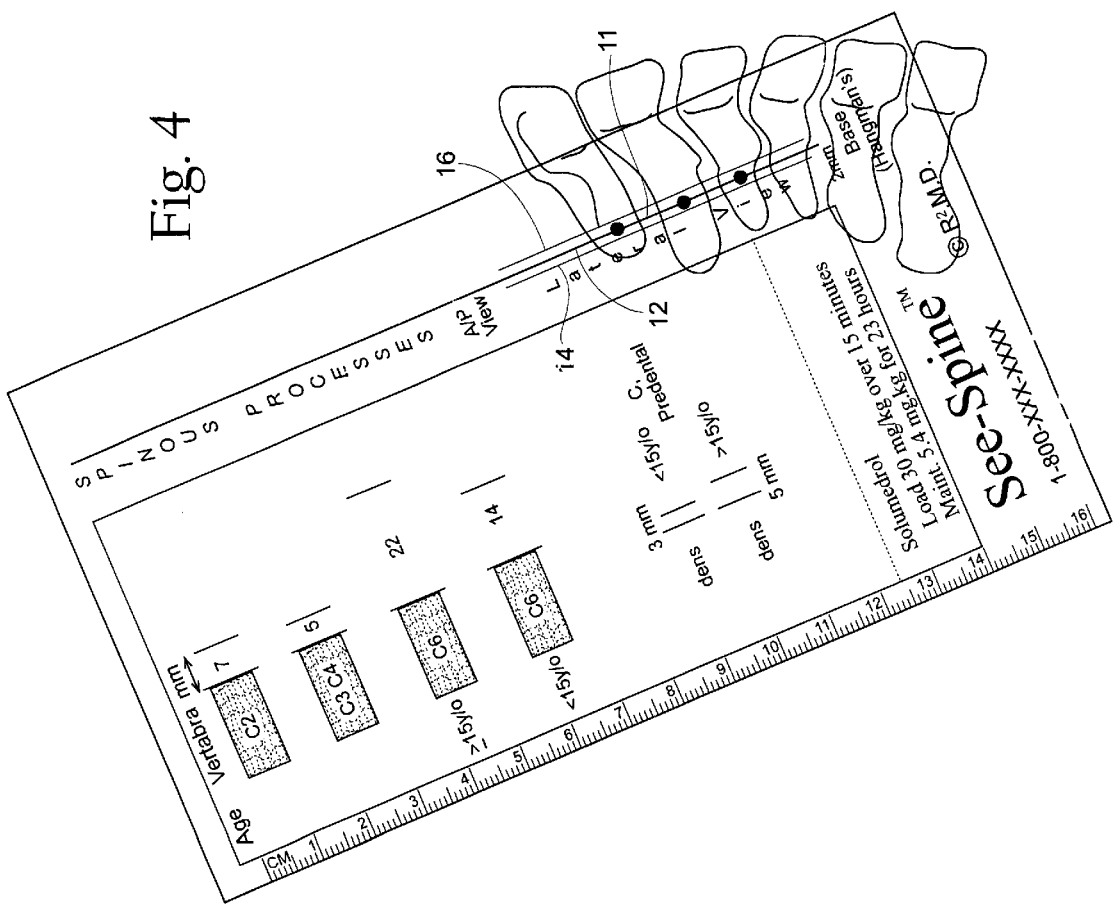
FIG. 4 is a top view showing the gauge of this invention overlaid on a radiographic film checking the posterior cervical line using the gauge.

A cervical spine gauge of this invention is shown in FIG. 1 generally indicated by numeral 10. FIG. 2 depicts a lateral view of several cervical vertebrae, namely C1–C4, inclusive. The predental space is indicated thereon relative to C1. Also illustrated is the posterior cervical line viewed laterally. The assessment of this posterior cervical line 11, utilizing gauge 10, is illustrated in FIG. 4. As noted in FIG. 1, a vertical line 12 is positioned between laterally displaced parallel vertical lines 14 and 16. A 2 millimeter (mm) spacing between each of the lines is provided. This enables easy assessment of the posterior cervical line on a radiographic image as seen in FIG. 4. If there is a displacement on this line greater than 2 mm, then the possibility of a hangman's fracture is suspected. Specifically, if the base of the spinous process of vertebra C2 lies more than 2 mm on either side of the posterior cervical line, the possibility of a hangman's fracture is suspected.

Figure 3:
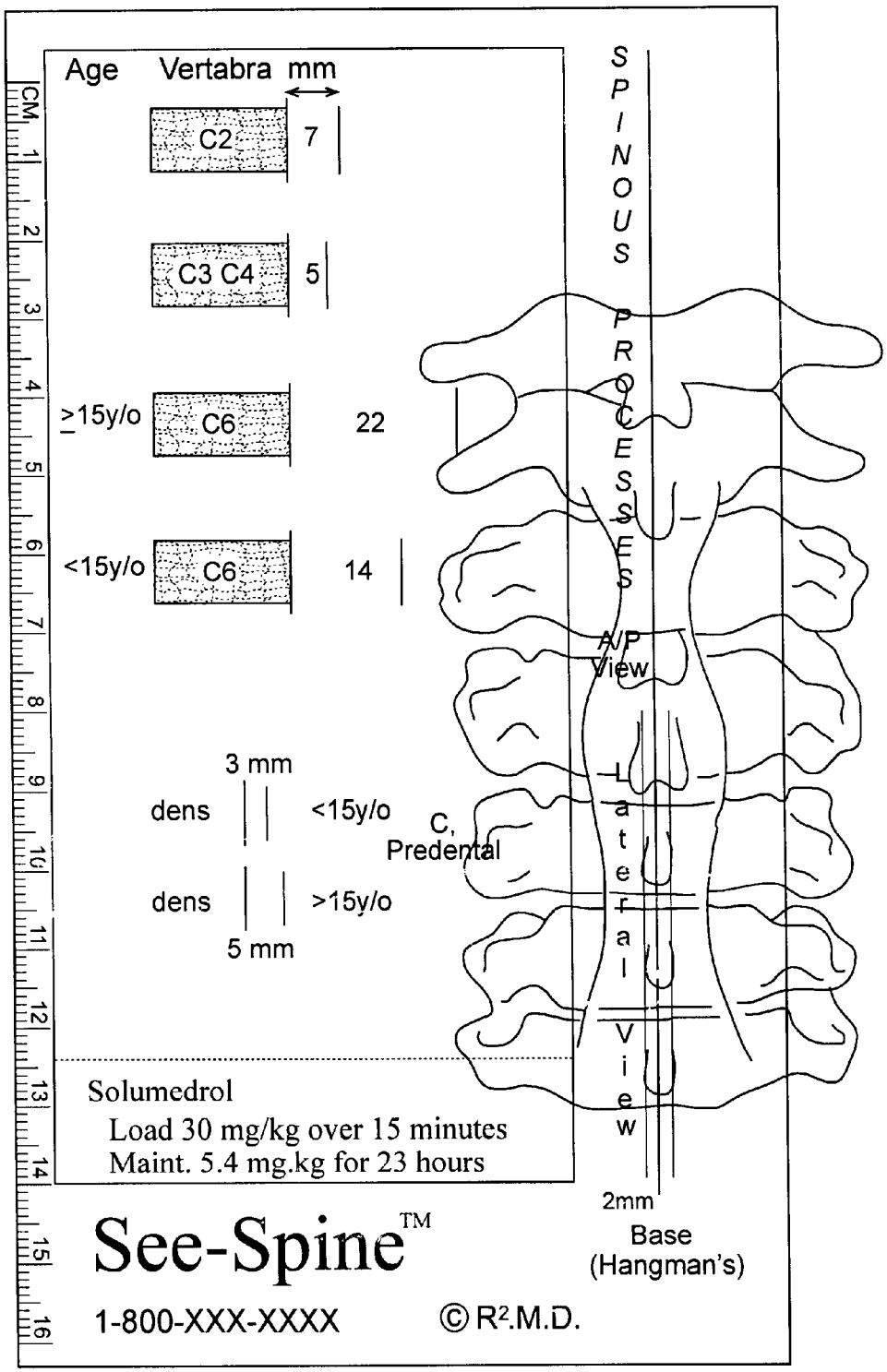
FIG. 3 is a view showing use of the gauge of FIG. 1 in checking alignment of spinous processes.

The line 12 also provides a guide for checking alignment of the spinous processes in a anterior-posterior view. The gauge 10 is overlaid on such an anterior-posterior view as seen in FIG. 3 over the middle of the spinous processes. Then, deviation from the straight line seen in FIG. 3 in either direction is indicative of the possibility of cervical injury. Also, as seen in FIG. 1, the gauge 10 has space thereon for information regarding dosages of commonly used medications, for example, Solumedrol (Methylprednisolone). Other, similar information can be provided instead, if desired.

Also, as a convenience to the health care professional, the gauge is provided with inscriptions 20 labeled "predental". These inscriptions provide a convenient means for measuring the amount of predental space in the radiographic image. In this respect, it is known that 3 mm is generally an average spacing for patients less than 15 years of age, whereas 5 mm is more typical for patients more than 15 years of age. These markings, thus, also are provided as a convenience to practitioners.

Figure 5:
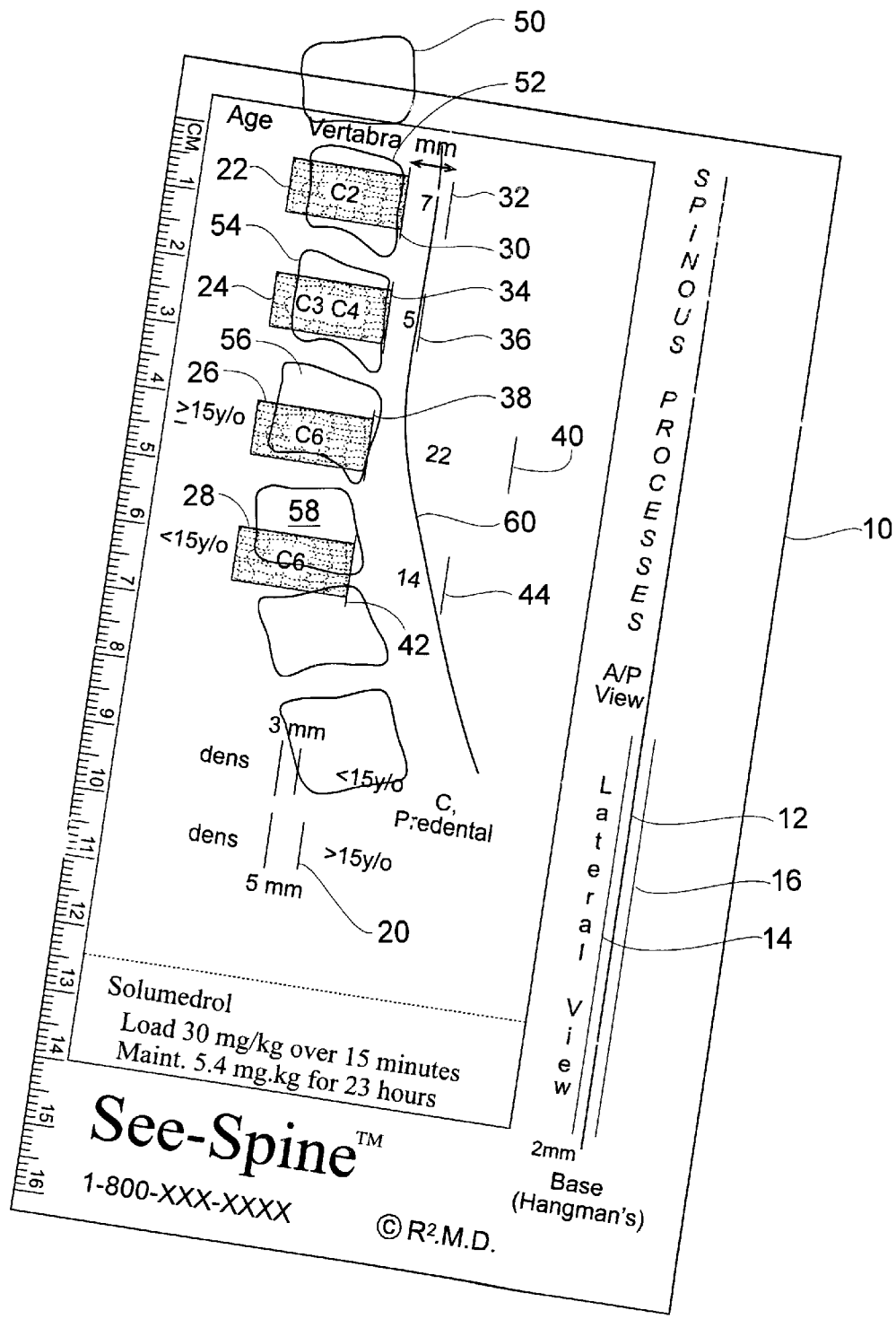
FIG. 5 is a view showing the gauge of this invention overlying a radiographic image and illustrating the analysis therewith of the C2–C4 vertebrae region.

Referring to FIG. 5 in conjunction with FIG. 1, there is seen on guide 10 a series of markings 22, 24, 26 and 28 representing specific vertebrae, as illustrated. In this case, image or inscription 22 represents vertebra C2. The inscription has an edge 30, representing the periphery of the C2 vertebra and a line 32 which is parallel to the edge 30. As indicated, the lines 30 and 32 have a measured space between them of 7 mm. Then, as seen in FIG. 5, when the gauge 10 is placed directly over a radiographic image 50 being a lateral radiographic image of a subject's spine. The image 50 is preferably back-lighted In this case, the image 22, representing vertebra C2 is placed directly over the radiographic image of the C2 vertebra with the edge 30 placed over and in alignment with the periphery of the radiographic image. In this example the image 52 represents the C2 vertebra. Also distinguishable is a line 60 on the radiographic image which is formed due to the soft tissue adjacent to the subject's spine. In the case, shown in FIG. 5, the image 60 extends between the lines 30 and 32 on the gauge, thus indicating soft tissue of less than 7 mm adjacent to the C2 vertebra. However, referring to the image 24, whose edge 34 is placed over the C3 vertebra, 54, it is noted that the soft tissue line 60 extends outside of the line 36 spaced 5 mm from the edge 34. Thus, in the case of the C3 vertebra 54, further inquiry might be made regarding the possibility of an injury. In a similar fashion, the images 56, 58, etc. of the other vertebrae are checked using the appropriate images 24, 26, or 28 of the gauge 10.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

What is claimed is:

1. A guide for assisting a health care practitioner in evaluating a lateral radiographic image of a spine comprising a flex transparent sheet, said sheet bearing at least one image thereon which image includes an edge representing the periphery of a vertebra, and a line inscribed thereon laterally displaced from said edge by a measured distance representing the maximum thickness of soft tissue allowed for said vertebra in the absence of a cervical spinal injury.

2. A guide according to claim 1 wherein a plurality of said images are inscribed on said flexible transparent sheet, each of said images representing a separate vertebra, and each having an edge representing the periphery of said separate vertebra, each said image having a line inscribed thereon which is laterally displaced from said edge by a measured distance representing the maximum thickness of soft tissue allowed for said specific vertebra represented by the image in the absence of a cervical spinal injury.

3. A process for evaluating a radiographic image of a spine, providing a guide comprising a flexible transparent sheet, said sheet bearing at least one image thereon which image includes an edge representing the periphery of a vertebra, and a line inscribed thereon laterally displaced from said edge by a measured distance representing the maximum thickness of soft tissue allowed for said vertebra in the absence of a cervical spinal injury placing said guide over a lateral radiographic image of a subject spine that is to be evaluated, with said edge placed in alignment with the image of a selected cervical vertebra corresponding to the image, and, observing the amount of soft tissue appearing in said radiographic image in relation to said line and thereby determining whether the amount of soft tissue present exceeds a soft tissue allowance for the specific vertebra.

4. Method according to claim 3 wherein a plurality of different vertebrae are evaluated in accordance with said process.

* * * * *